United States Patent

Tietje-Girault et al.

[11] Patent Number: 5,575,930
[45] Date of Patent: Nov. 19, 1996

[54] METHOD OF MAKING GAS PERMEABLE MEMBRANES FOR AMPEROMETRIC GAS ELECTRODES

[76] Inventors: Jordis Tietje-Girault, 1088 Ropraz, En Vernay, Switzerland; Brian J. Seddon, Chemin De Fonadel 37 Prilly, Lausanne, CH1008, Switzerland; Jerome F. McAleer, 52 Nobles, Grove, Wantage, Oxfordshire OX12 ONR, United Kingdom

[21] Appl. No.: 407,002
[22] PCT Filed: Oct. 6, 1993
[86] PCT No.: PCT/GB93/02076
  § 371 Date: Mar. 27, 1995
  § 102(e) Date: Mar. 27, 1995
[87] PCT Pub. No.: WO94/08236
  PCT Pub. Date: Apr. 14, 1994

[30] Foreign Application Priority Data

Oct. 7, 1992 [GB] United Kingdom ............. 9221099

[51] Int. Cl.[6] ............................................. B23K 26/00
[52] U.S. Cl. ............... 216/65; 204/415; 205/783; 216/72; 216/75
[58] Field of Search ................ 204/153.18, 415; 205/782.5, 783; 216/65–67, 72, 74, 75, 100

[56] References Cited

U.S. PATENT DOCUMENTS

| | | | |
|---|---|---|---|
| 3,239,444 | 3/1966 | Heldenbrand | 204/415 |
| 3,510,420 | 5/1970 | Mills | 204/415 |
| 3,838,033 | 9/1974 | Mindt | 204/415 |
| 4,214,966 | 7/1980 | Mahoney | 216/66 |
| 4,275,286 | 6/1981 | Hackett | 216/66 |
| 4,388,166 | 6/1983 | Suzuki et al. | 204/415 |
| 4,490,211 | 12/1984 | Chen et al. | 216/65 |
| 5,104,480 | 4/1992 | Wojnarowski et al. | 216/65 |

FOREIGN PATENT DOCUMENTS

| | | |
|---|---|---|
| 0154982 | 9/1985 | European Pat. Off. . |
| 0237914 | 9/1987 | European Pat. Off. . |
| 0494382A1 | 7/1992 | European Pat. Off. . |
| 3247722 | 6/1984 | Germany . |
| WO91/08474 | 6/1991 | WIPO . |

*Primary Examiner*—T. Tung
*Attorney, Agent, or Firm*—Howson and Howson

[57] ABSTRACT

A method of manufacturing a gas-permeable membrane for an amperometric gas electrode comprising demetallizing areas of a metallized film to obtain a regular array of gas-permeable micropores.

14 Claims, 3 Drawing Sheets

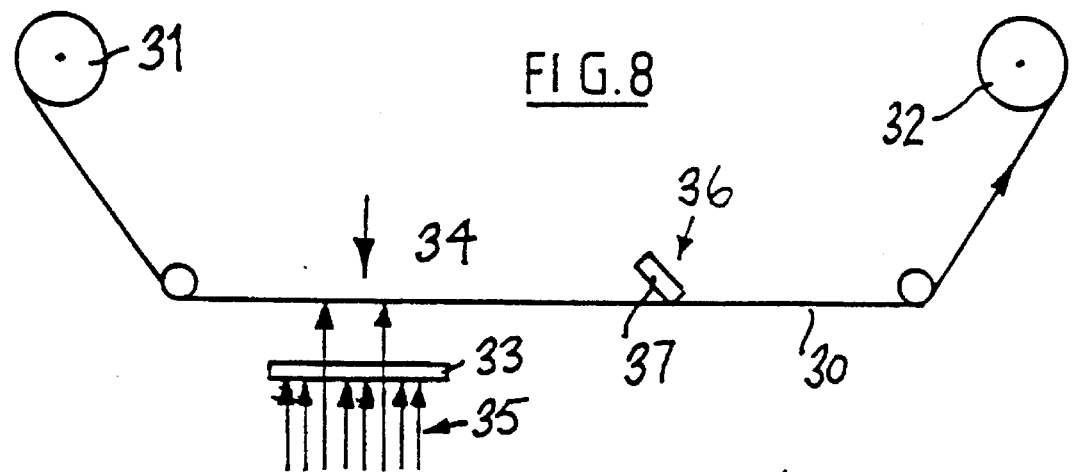
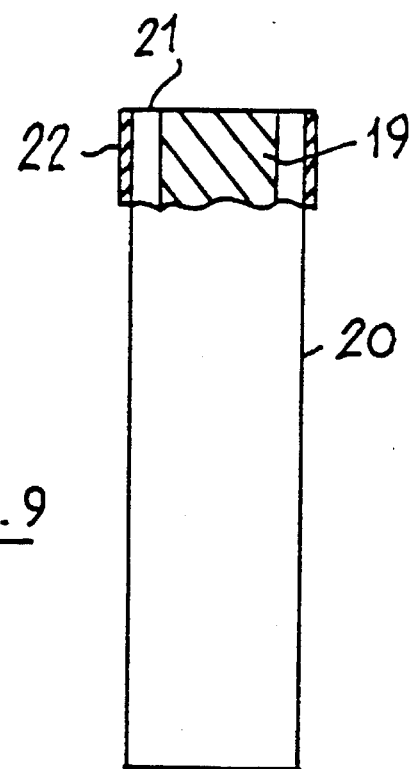
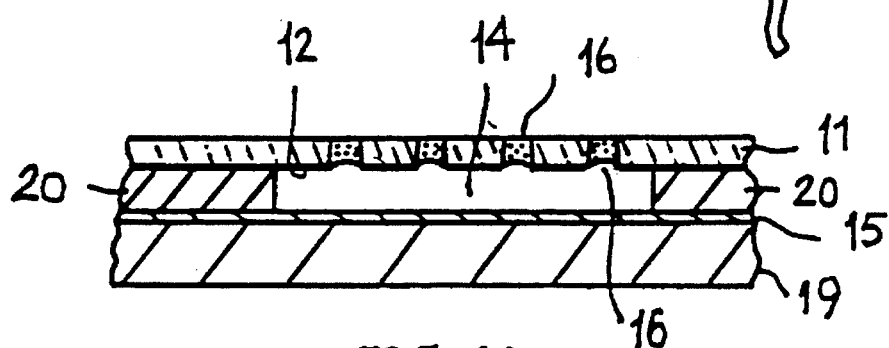

METHOD OF MAKING GAS PERMEABLE MEMBRANES FOR AMPEROMETRIC GAS ELECTRODES

BACKGROUND OF THE INVENTION

1. Field of the Invention

The electrochemical amperometric detection of redox gases such as oxygen is a well established technique, and the electrode used in such a technique is often referred to as a "Clark Electrode". In the case of an oxygen Clark Electrode, this detection is based on oxygen transport through a gas-permeable membrane to an enclosed electrolyte solution, and the subsequent reduction of oxygen dissolved in this solution, usually on a platinum or gold sensing electrode. The potential of this sensing electrode is held at negative potential compared to the potential of the electrolyte solution by use of a reference electrode, classically a silver/silver chloride electrode. A schematic diagram illustrating this conventional approach is shown in FIG. 1 of the accompanying drawings.

The response time of classical detection devices, where the sensing electrode, on which the electrochemical reaction takes place, is separated from the gas-permeable membrane by a thin (e.g. a submillimeter thick) layer of electrolyte solution, is more than 100 seconds. The response time is limited by the linear diffusion rate of the redox gas through the gas-permeable membrane and into the electrolyte solution as depicted in FIG. 1.

The present invention is based on the use of gas-permeable polymer films (for example films a few microns thick of e.g. polypropylene or polyester) metallized on one side (e.g. with gold or platinum). Such metallized films are commercially available and are currently used in the food packaging industry.

At the heart of the present invention is the use of a novel type of composite gas-permeable membrane which has been manufactured by demetallizing (e.g. by using UV excimer laser photoablation) areas of a metallized polymer film, to obtain a regular array of gas-permeable micropores each having a diameter or width of a few microns. The micropores can be in the form of microdiscs and/or microbands, since the shape of each area is of secondary importance.

2. Description of the Related Art

Our prior International application published as WO 9108474 discloses the use of photoablation for the creation of apertures in electrically insulating material when creating microelectrodes and EP-A-0494382 discloses the creation of an electrochemical cell in which photoablation is used to drill holes in an insulating substrate of the cell and to expose metallized areas on the substrate. EP-A-0494382 does disclose a gas-permeable membrane but not one subjected to subsequent thinning (e.g. by photoablation).

SUMMARY OF THE INVENTION

According to one aspect of the invention there is provided a method of manufacturing a gas-permeable membrane for an amperometric gas electrode from a polymer film metallized on one surface thereof which method comprises demetallizing areas of the metallized film to obtain a regular array of gas-permeable micropores having a diameter or width of a few microns.

The polymer film can be inherently gas-permeable when demetallized, but if made of non-permeable material can be made gas-permeable over the localised areas where demetallization is effected.

Conveniently, the regular array of micropores is obtained by excimer laser photoablation, preferably using a UV excimer laser. The metallized film is desirably of gold or platinum and the polymer film preferably is polypropylene or polyester.

Suitably each micropore comprises a porous plug replacing film material removed in the demetallizing process.

An amperometric gas electrode made by the method of the invention represents a further aspect of this invention as do disposable devices using such electrodes and incorporating enzymes or microbes for controlled biological testing methods.

BRIEF DESCRIPTION OF THE DRAWINGS

The invention will now be further described, by way of example, with reference to the accompanying drawings, in which:

FIG. 8 shows one method of making an electrode membrane for use in the electrodes of FIGS. 2 and 4, FIG. 9 schematically illustrates one form of electrode mounted on a support, and FIG. 10 is an enlarged sectional view of a modified arrangement of electrode and support therefor.

DESCRIPTION OF PREFERRED EMBODIMENTS

Figure 1:
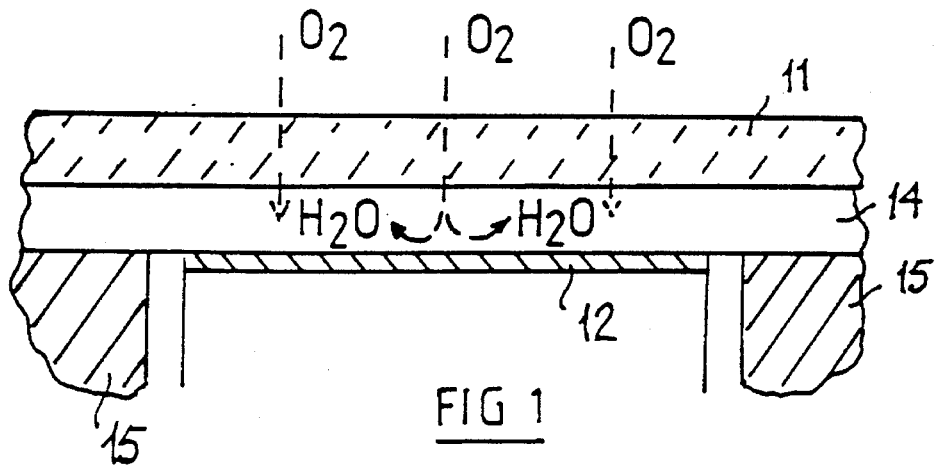
FIG. 1 is a schematic view of a classical amperometric oxygen electrode.

As already discussed FIG. 1 illustrates a prior art arrangement in which the oxygen gas permeates through a permeable membrane 11 into an electrolyte solution 14 where chemical reaction occurs in the presence of a sensing electrode 12 and reference electrodes 15.

Figure 2:
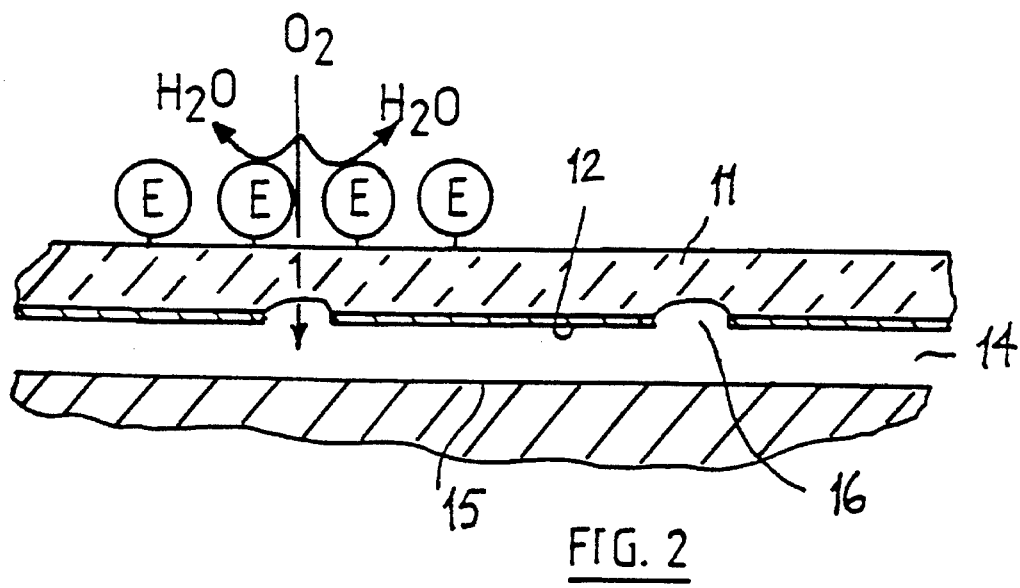
FIG. 2 is a schematic view of a first embodiment of electrode in accordance with this invention.

An oxygen electrode device according to the present invention which includes a novel gas-permeable membrane is illustrated in FIG. 2 and comprises a gas-permeable polymer film 11 having a metallic electrode layer 12 provided with demetallized microareas 16, a thin layer of an electrolyte solution 14 and a reference electrode 15 which can be a silver/silver chloride electrode.

Because oxygen cannot permeate through the metallic layer 12, oxygen flow between the analyte and the internal electrolyte solution 14, can only occur through the demetallized microareas 16. The oxygen flowing through these areas can then be classically electrochemically reduced. The collection efficiency of the metallic electrode layer 12, e.g. of gold or platinum, for the reduction of the oncoming oxygen is very high due to the micronic dimension of the demetallized areas. Furthermore, the electrode layer 12 cannot be closer to the membrane 11 than in the arrangement illustrated, and therefore the need for diffusion of oxygen through the electrolyte solution 14 is obviated. Both of these innovative features combine to provide improvements in the oxygen electrode performance.

Figure 3:
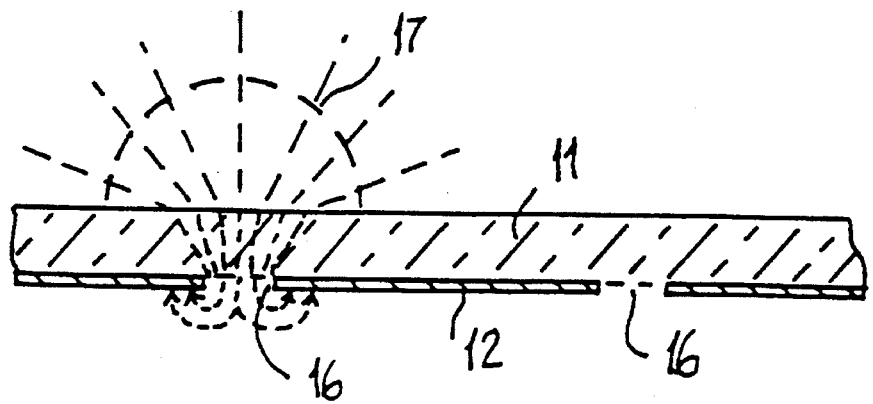
FIG. 3 is a view of the diffusion field applicable to an electrode as shown in FIG. 2, FIGS. 4 and 5 are views corresponding to FIGS. 2 and 3 applicable to a second embodiment of electrode in accordance with the invention.

The flux of oxygen through the gas-permeable membrane 11 however is not homogeneous as in a classical oxygen electrode (employing flux by linear diffusion as shown by dashed line arrows in FIG. 1) but converges to each demetalized microarea 16 as shown by the dashed-line arrows in FIG. 3. In the case of the microareas 16 being microdiscs, this results in a pseudo hemispherical diffusion regime, where each demetallized microdisc 16 acts as a sink for the oxygen present in a hemispherical diffusion shell 17 above it, an arrangement expected to lead to a steady sate flux of oxygen with reduced dependence on the flow of the analyte above the membrane 11. The oxygen flux density through the microdisc 16 is much higher than that provided by simple linear diffusion processes; thus providing higher local oxygen concentration near the reducing electrode 12.

A further advantage of a manufacturing method according to this invention is that the thickness of the gas-permeable membrane 11 can be reduced by the demetallizing process (e.g. if more laser pulses than those necessary for a demetalization photoablation process are used). This allows further tailoring of the permeation properties of the membrane 11 and therefore leads to a reduction of the response time of the electrode device.

Figure 4:
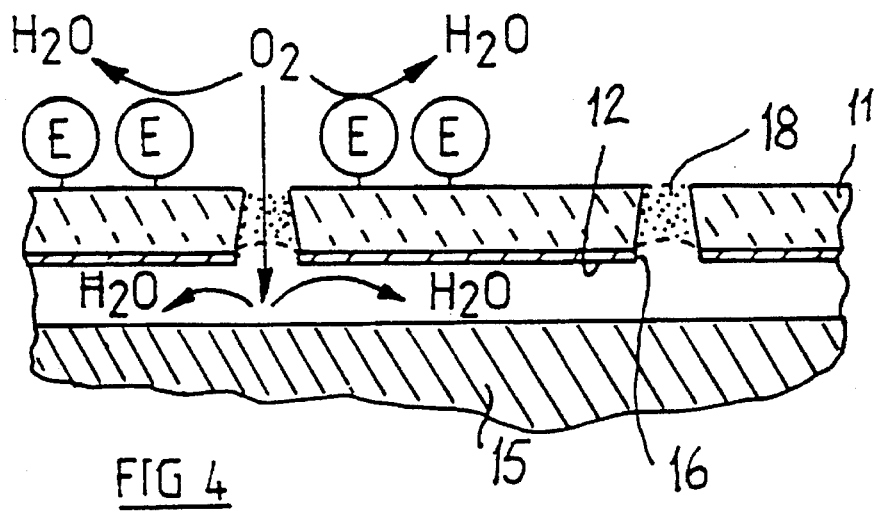
Figure 5:
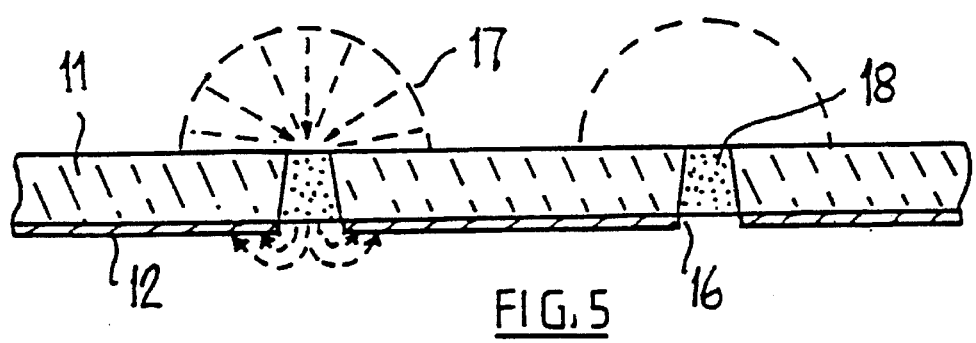

A modification of the invention is to use the same demetallizing agent (e.g. a UV excimer laser photoablation system), not only to demetallize over the required areal pattern but also to drill at least partly through the thin polymer layer. When drilling fully through the polymer film (as shown in FIG. 4) it is not necessary to use a gas-permeable polymer film since the microhole arrangement so created can then be filled by a plug 18 of a phase which is highly oxygen permeable, e.g. a plug of silicon material. This hole filling or plugging procedure can be carried out, for example, by a screen printing method or a casting method. In this modified approach, the array of filled microholes represent an array of oxygen micropores and because the dimensions of the filled microholes are on the micron scale, the diffusion of oxygen to these microdiscs is controlled by a regime of part-spherical diffusion similar to that observed for the diffusion of reactants to a microdisc electrode array of similar dimensions created in a still coherent gas-permeable film as shown in FIG. 2.

The difference in the gas diffusion fields between the classical case, i.e. linear diffusion, and the part-spherical gas diffusion field which arises with the use of an electrode according to this invention is thought to be the main source of the advantages achieved by the present patent application indeed, linear gas diffusion fields cannot yield steady state regimes and any technique based on this type of mass transfer requires a calibration procedure. In contrast, the use of a part-spherical diffusion field is by nature much more efficient as it gathers redox gas from a wider volume, and consequently yields a steady state gas diffusion field. In the case of the amperometric determination of oxygen, this means the generation of a constant reduction current which is a function of the geometry of the device, the diffusion coefficient of oxygen (which is a function of temperature) and the concentration it is wished to measure. If the geometry of the electrode device and the temperature are known, then the concentration can be directly and accurately calculated without resorting to time-consuming calibration procedures.

This generic proposed method for the amperometric detection of oxygen is particularly well suited for the design of biosensors where an enzyme (E), say glucose oxidase, competes with the device for the oxygen dissolved in the analyte. Many biosensors based on the classical oxygen electrode have been proposed. The response of the devices hitherto proposed is limited by the physical distance between the enzymes, the membrane and the electrode. By the nature of the proposed novel design, the enzymes can be immobilized on the thin polymer film. In this way, the distance between the enzyme-membrane and the membrane-electrode is reduced which in turn results in a reduced response time. Although enzymes can also be immobilized on the gas-permeable membrane of a classical "Clark Electrode", they tend to hinder the linear flux of oxygen. In the case of an electrode according to this invention however, the "active" surface, i.e. the surface area directly above the demetallized microdiscs represents less than 1% of the total surface area, yet the part-spherical diffusion fields can be arranged to cover the majority of the sensor surface by an appropriate choice of the density of the array of micropores. It is possible to limit the enzyme immobilization in areas not overlaying the demetallized microareas by using the modified approach of creating filled micropores. Indeed, the difference in materials used for the membrane 11 and the micropore filling material phase 18 allows the enzyme immobilization to occur only on the film but not on the micropore filling phase.

Coupling with oxidases

Numerous analytes can be determined via oxygen depletion in the presence of the appropriate enzyme. For example, cholesterol reacts with oxygen in the presence of cholesterol oxidase to form cholestenone. The rate of this reaction depends on the concentrations of enzyme and substrate and on the partial pressure of oxygen in the sample. Thus a simple device for determining cholesterol would comprise an electrode or array of electrodes for determining the background oxygen tension and an enzyme modified array for determining oxygen tension in the presence of the enzyme reaction (i.e. in the manner shown in FIG. 3). The enzyme could be immobilized onto local areas of the surface of the gas membrane or alternatively the sensor could comprise two compartments, one containing the enzyme and one without. The cholesterol concentration would conveniently be calculated by comparing the oxygen responses on the two parts of the sensor. The same principle could be used to determine many other analytes. for example glucose (using glucose oxidase), phenols (using polyphenol oxidase), xanthine (using xanthine oxidase) and so on.

Figure 6:
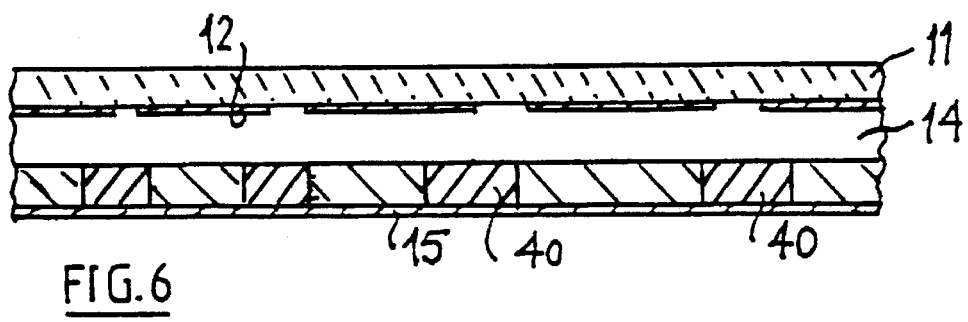
FIG. 6 is a schematic sectional side view of a composite gas-liquid-liquid electrode in accordance with the invention.

Similarly, other analytes can be determined by the amperometric detection of enzymically produced ammonia. Examples are urea (using urease) and creatinine using creatinine imminase. The amperometric determination of ammonia can be effected either by inclusion of a redox marker species such as bromocresol green in an electrolyte solution 14 shown in FIG. 6 or by transfer of the ammonium ion across a supported liquid-liquid interface. In FIG. 6, ammonia diffuses across a gas-permeable membrane 11 and dissolves as ammonium ions in the electrolyte solutions in the aqueous phase 14. Each ammonium ion is then driven across the interface into a supported non-aqueous phase 40 by the application of an appropriate potential difference between the electrodes 12 and 15. The ammonia concentration can then be calculated from the ion transfer current.

Biological Oxygen Demand

In specific embodiments of a device according to the invention an oxygen electrode can be used in conjunction with microbes to determine biological oxygen demand (BOD) or toxicity. Thus in FIG. 7 the respiration rate of microbes (e.g. freeze-dried microbes) held in a layer 41 in close proximity with a gas-permeable membrane 11 is determined by the BOD of the sample. A high BOD will result in a rapidly changing oxygen tension whereas a low BOD will result in a fairly constant oxygen measurement. One of the main advantages the micro-electrode configuration brings to this measurement is that the micro-electrode itself consumes very little oxygen and so does not perturb the measurement. A total toxicity test kit would include a layer 41 loaded with microbes and nutrient next to the gas-permeable membrane. Since both of these devices measure oxygen depletion in the sample, a sample chamber 42 is included to minimize oxygen ingress from the atmosphere.

An oxygen electrode or biosensor in accordance with this invention can be manufactured by a continuous reel to reel process, as shown in FIG. 8 where a web 30 of metallized film passes from a supply spool 31 to a wind-up spool 32. In its passage between spools a pattern of apertures set by a mask 33 is formed in the web 30 by photoablation at a station 34 using ultra violet laser light 35 from a source not shown. The ablation can be effected "on the fly" or in a dwell period following each advance of the web by a pre-set amount. Downstream of the photoablation station 34 is a hole-filling station 36 where the holes formed in the web at station 34 are filled with an appropriate plug of gas-permeable material. A squeegee 37 schematically illustrates this stage.

Figure 7:
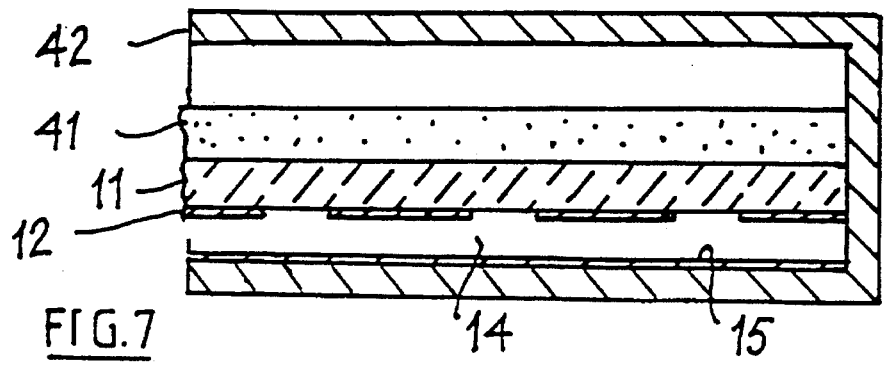
FIG. 7 is a schematic cross-sectional view of a cell for determining BOD or sample toxicity according to the invention.

In addition to the two types of system discussed in FIGS. 6 and 7 further systems are possible using a filled web as created by the process shown in FIG. 8.

Firstly, a stick electrode approach can be employed where the film is secured to (e.g. clipped on) a body containing the reference electrode, and the electrolyte solution; very much like a prior art commercially available oxygen electrode. The main difference being that the platinum or gold electrode on which the electrochemical reduction takes place is attached to the gas-permeable membrane, and that therefore electrical contact should be made to the latter (see FIG. 9). In FIG. 9 the reference electrode is shown at 19, the containing body at 20, and a metal contact to the metallized film of membrane 21 is shown at 22. Neither the film nor the clip is shown in FIG. 9.

FIG. 10 shows an arrangement in which a web 11 of polymer film having a working electrode 12 on its lower face and containing plugged micropores 16 is supported above a support 19 carrying a reference electrode 15. Spacers 20 of dielectric material hold electrodes 12 and 15 apart to contain a layer of electrolyte 14 therebetween. Both of the electrodes 12 and 15 and the spacers 20 can be created by screen printing and the electrolyte solution can also be printed as part of the process (i.e. it can be in the form of an aqueous gel or hydrogel).

We claim:

1. A method of manufacturing a gas-permeable membrane for an amperometric gas electrode from a polymer film metallized on one surface thereof which method comprises demetallizing areas of the metallized film to obtain a regular array of gas-permeable micropores.

2. A method according to claim 1, in which the polymer film is inherently gas-permeable.

3. A method according to claim 2, in which the regular array of micropores is obtained by excimer laser protoblation.

4. A method according to claim 3, in which the metallized layer on the polymer film is gold or platinum.

5. A method according to claim 4, in which the polymer film is polypropylene or polyester.

6. A method according to claim 1, in which the polymer film is of non gas-permeable material but is rendered gas-permeable over areas corresponding to said regular array of micropores.

7. A method according to claim 6, in which the regular array of micropores is obtained by excimer laser protoblation.

8. A method according to claim 7, in which the metallized layer on the polymer film is gold or platinum.

9. A method according to claim 1, in which the regular array of micropores is obtained by excimer laser photoablation.

10. A method according to claim 9, in which the photoablation involves the use of a UV excimer laser.

11. A method according to claim 10, in which the metallized layer on the polymer film is gold or platinum.

12. A method according to claim 11, in which the polymer film is polypropylene or polyester.

13. A method according to claim 1, in which the metallized layer on the polymer film is of gold or platinum.

14. A method according to claim 1, in which the polymer film is polypropylene or polyester.

* * * * *